United States Patent [19]

Parks

[11] 3,962,422
[45] June 8, 1976

[54] METHOD FOR IMMUNIZING NURSING PIGLETS AGAINST TRANSMISSIBLE GASTROENTERITIS(TGE) VIRUS

[75] Inventor: John B. Parks, Mountain View, Calif.

[73] Assignee: Syntex (U.S.A.) Inc., Palo Alto, Calif.

[22] Filed: Feb. 18, 1975

[21] Appl. No.: 550,319

[52] U.S. Cl. .................................. 424/89; 424/86
[51] Int. Cl.² .................. A61K 39/12; A61K 39/42
[58] Field of Search ..................................... 424/89

[56] References Cited
UNITED STATES PATENTS

| | | | |
|---|---|---|---|
| 3,127,318 | 3/1964 | Eversole et al. | 424/89 |
| 3,479,430 | 11/1969 | Welter | 424/89 |
| 3,519,710 | 7/1970 | Bass | 424/89 |
| 3,585,108 | 6/1971 | Welter | 195/1.3 |
| 3,704,203 | 11/1972 | Welter | 195/1.3 |
| 3,823,228 | 7/1974 | Ferris et al. | 424/89 X |

OTHER PUBLICATIONS

Bohl, E. H. et al., Infection & Immunity 6 (3): 289-301 (Sept. 1972) "Antibody Responses in Serum, Colostrum and Milk of Swine After Infection or Vaccination with Transmissible Gastroentoritis Virus".
Saif, L. J. et al., Infection & Immunity 6 (4) : 600–609 (Oct. 1972) "Isolation of Porcine Immunoglobulins and Determination of the Immunoglobulin Classes of Transmissible Gastroentoritis Viral Antibodies".
Benyeda, J. et al., Vet. Bull. 44 (8) No. 3735, Aug. 1974 "Immunization Against Transmissible Gastroenteritis II, Persistence of Antibody and Effect of Revaccination".
Mocsari, E. et al., Vet. Bull. 44 (12) No. 5954, Dec. 1974 "Immunization Against Transmissible Gastroenteritis IV, Antibody Formation in Sows Immunized Twice".

Primary Examiner—Shep K. Rose
Attorney, Agent, or Firm—Gerard A. Blaufarb; William B. Walker

[57] ABSTRACT

Method for immunizing nursing piglets against transmissible gastroenteritis (TGE) virus by administering to the pregnant sow an effective amount of a vaccine containing attenuated TGE virus and permitting the nursing piglets to suckle the sow. The vaccine is administered twice, (a) intramuscularly at from about 63 days to about 21 days pre-farrowing and (b) intranasally at from about 21 days to about 7 days pre-farrowing, with the proviso that at least 14 days and not more than 42 days elapse between the intranasal and intramuscular inoculations.

6 Claims, No Drawings

3,962,422

METHOD FOR IMMUNIZING NURSING PIGLETS AGAINST TRANSMISSIBLE GASTROENTERITIS(TGE) VIRUS

BRIEF SUMMARY OF THE INVENTION

This invention relates to a novel method of immunizing nursing piglets against transmissible gastroenteritis (TGE) virus by administering to a pregnant sow an effective amount of a vaccine containing attenuated TGE virus, said vaccine being administered twice, (a) intramuscularly at from about 63 days to about 21 days pre-farrowing and (b) intranasally at from about 21 days to about 7 days pre-farrowing, with the proviso that at least 14 days and not more than 42 days elapse between the intranasal and intramuscular inoculations, and permitting said nursing piglets to suckle said sow.

PRIOR ART

Bohl et al., Infection and Immunity, September 6, 1972, p. 289–301 and Saif et al., Infection and Immunity, Oct. 6, 1972, p. 600–609, have reported that (1) there is high mortality in challenged nursing piglets when attenuated strains of TGE virus are administered to pregnant sows intramuscularly and (2) nursing piglets are better protected when virulent TGE virus was orally-intranasally administered to pregnant sows. Abou-Youssef et al., Proceedings of the 75th Annual Meeting of the United States Animal Health Association, 1971, p. 329–341, have reported that nursing piglets were not protected when virulent TGE virus was administered intramuscularly to the pregnant sow; but when virulent TGE virus was administered orally to pregnant sows, the nursing piglets were protected. However, Stone et al., American Journal of Veterinary Research, 35, Mar. 3, 1974, p. 339–345, have reported that pregnant sows inoculated either orally or intramuscularly with virulent TGE virus afforded protection to the nursing piglets. Thus, it will be seen that there is disagreement in the art regarding both the type of virus (virulent or attenuated ) to be administered and the mode of administration.

DETAILED DESCRIPTION OF THE INVENTION

This invention relates to a method for the immunization of nursing piglets against transmissible gastroenteritis (TGE). More particularly it relates to a method for imparting immunity to nursing piglets against TGE virus by vaccinating the pregnant sow, the dam, twice (a) intramuscularly from about 63 days to about 21 days pre-farrowing and (b) intranasally from about 21 days to about 7 days pre-farrowing, with the proviso that at least 14 days and not more than 42 days elapse between the intranasal and intramuscular inoculations, and permitting said nursing piglets to suckle their dam.

TGE in pigs is an easily transmissible, viral, enteric disease. In unimmunized nursing younger piglets (usually less than two weeks of age) it is characterized by severe diarrhea and high mortality and morbidity rates. From birth through the first two weeks of life, nursing piglets are extremely susceptible to TGE virus since they have not yet built up their own immunity.

It is not economically feasible to individually immunize each nursing piglet because of the large amount of husbandry involved and the increased labor costs involved therein. Even in those instances where the pregnant sow has been vaccinated intramuscularly and transmits the immunity which it has developed to the nursing piglets, via the colostrum and milk, the mortality (usually of the order of 20–40%) and morbidity are still high.

It is readily apparent that the financial losses engendered by the mortality and morbidity of nursing piglets represents a severe economic problem confronting the pig husbandryman.

It has now been found that the incidence of mortality and morbidity in nursing piglets is markedly reduced by the procedure of immunizing them according to the novel method described above and more fully below.

Pregnant sows are intramuscularly inoculated with attenuated TGE virus at from about 63 days to about 21 days pre-farrowing. This first inoculation is followed by a second inoculation of attenuated TGE virus vaccine, intranasally, at from about 21 days to about 7 days pre-farrowing, with the proviso that at least 14 days and not more than 42 days elapse between the intranasal and intramuscular inoculations. The amounts and type of attenuated TGE virus vaccine administered intramuscularly and intranasally are not critical and can be varied within wide limits, so long as the administration thereof is sufficient to produce immunity in the nursing piglets, the desired result. Those skilled in the art will easily recognize that the amount of attenuated TGE virus vaccine to be administered, intramuscularly and intranasally, is a function of the potency of the particular attenuated TGE virus vaccine used. The attenuated TGE virus vaccine should contain at least 10,000 $TCID_{50, s}$ (Tissue Culture Infective Dose) of TGE virus and usually contains from about 50,000 to about 1,000,000 $TCID_{50, s}$ of TGE virus.

Preferably, pregnant sows are intramuscularly inoculated with attenuated TGE virus vaccine containing from about 50,000 to about 1,000,000 $TCID_{50, s}$ of TGE virus at from about 49 days to about 35 days pre-farrowing. This first inoculation is followed by a second inoculation, intranasally, with attenuated TGE virus vaccine containing from about 50,000 to about 1,000,000 $TCID_{50, s}$ of TGE virus at from about 18 days to about 10 days pre-farrowing.

The most preferred attenuated TGE virus vaccine is that prepared according to U.S. Pat. No. 3,479,430 (see also U.S. Pat. Nos. 3,585,108 and 3,704,203), which is hereby incorporated by reference and made a part hereof, containing from about 50,000 to about 1,000,000 $TCID_{50, s}$ of TGE virus; and the most preferred time of administration for the intramuscular and intranasal inoculations are 42 days pre-farrowing and 14 days pre-farrowing, respectively.

The volume of the attenuated TGE virus vaccine is not critical, preferably from about 1 ml. to about 10 ml., so long as said volume of vaccine contains at least 10,000 $TCID_{50, s}$ of TGE virus.

Following farrowing the nursing piglets are left corraled with, and permitted to suckle their dams, thus avoiding the necessity of handling them in order to immunize them.

The exact mechanism(s) by which the immunity to TGE virus is transferred from the intramuscularly intransally inoculated pregnant sow to her nursing piglets, via the colostrum and milk, has not been fully elucidated.

However, as shown by the data in Example 1 all three types of immunoglobulins (IgM, IgA and IgG) are produced in the colostrum of sows inoculated orally (Group C) with virulent TGE virus (except for Fraction VI) or sows inoculated intramuscularly (Group A)

or intranasally (Group B) with attenuated TGE virus vaccine, and Fraction III contains almost half of the neutralizing activity for Groups B and C as represented by IgA, which immunoglobulin has been found to most effectively impart protection to piglets; and as shown by the data in Example 2, the average titers of TGE virus neutralizing activity in colostrum and/or milk were higher in the sows inoculated intramuscularly intranasally (Group 2) than the sows inoculated intramuscularly intramuscularly (Group 1) and that the titers declined less rapidly in the Group 2 sows than in the Group 1 sows (Table III), and that the mortality and morbidity of the Group 1 nursing piglets was approximately three times greater than the Group 2 nursing piglets (Table IV).

DESCRIPTION OF SPECIFIC EMBODIMENTS

The following specific description, recited in the examples below, is given to enable those skilled in this art to more clearly understand and practice the present invention. It should not be considered as a limitation upon the scope of the invention but merely as being illustrative and representative thereof.

The Group A, B and C pooled samples were then separately fractionated on Sephadex G-200 (Pharmacia-Fine Chemicals AB, Uppsala, Sweden) and six fractions were collected from each of the pooled samples. (The Sephadex G-200 fractionation separates molecules based on the size providing preliminary separation of the various immunoglobulin classes. Immunoglobulin M (IgM), the largest in size was found in the first and second fractions, immunoglobulin A (IgA), intermediate in size was found in the second third and fourth fractions and immunoglobulin G (IgA), the smallest in size, and the last to be eluted, was found in the fourth, fifth and sixth fractions.)

The in vitro TGE virus neutralizing activity of each fraction from each group was determined, based upon the standard serum neutralization test [See Paul et al., Virus and Rickettsial Diseases, 2nd Ed., American Public Health Association Press, New York, N.Y., (1956), p.53] utilizing the microtiter system in which 251.2 $TCID_{50}$, $_s$ (TCID is Tissue Culture Infective Dose) of TGE virus is employed. The results expressed as percent of TGE virus neutralizing activity in each fraction of pooled colostrum, are set forth in Table 1.

TABLE 1

Percent of TGE Virus Neutralizing Activity in Each Fraction of Pooled Colostrum

| Virus | Vaccination Route of Pregnant Sows | I | II | III | IV | V | VI |
|---|---|---|---|---|---|---|---|
| Group A (4 Sows) Attenuated TGE | Intramuscular | 5 | 8 | 11 | 29 | 35 | 12 |
| Group B (1 Sow) Attenuated TGE | Intranasal | 3 | 13 | 51 | 23 | 6 | 4 |
| Group C (2 Sows) Virulent TGE | Oral | 9 | 9 | 46 | 19 | 17 | 0 |
| Immunoglobulin Distribution | | | IgM | IgA | | IgG | |

EXAMPLE 1

Seven pregnant sows, serologically negative to TGE virus, were divided into three groups. The group A animals, consisting of 4 sows, were inoculated intramuscularly twice, 42 days and 14 days pre-farrowing, with 2 ml. of an attenuated strain of TGE virus vaccine (TGE-Vac, Diamond Laboratories, Inc., Des Moines, Iowa 50304), prepared according to the method described in U.S. Pat. No. 3,479,430 (see also U.S. Pat. Nos. 3,585,108 and 3,704,203 for the same method of preparation of vaccine) containing 676,083 $TCID_{50}$, $_s$ of TGE virus. The Group B animals consisting of 1 sow, was inoculated intranasally twice, 42 days and 14 days pre-farrowing, with the same vaccine used for the intramuscular inoculation of Group A. The Group C control animals, consisting of 2 sows, were orally inoculated twice, 42 days and 14 days prefarrowing, with 5 ml. of virulent TGE (Miller strain No. 3) containing 1000 $LD_{50}$, $_s$ (LD=Lethal Dose for piglets) of TGE virus.

Three days post-farrowing a sample of colostrum (50 ml.) was taken from each sow. The colostrum samples taken from the Group A sows were pooled, as were the colostrum samples taken from the Group B and C sows.

EXAMPLE 2

Eleven pregnant sows, serologically negative to TGE virus were divided into three groups. The Group 1 animals, consisting of 4 sows, were inoculated intramuscularly twice, 42 days prefarrowing and 14 days pre-farrowing, with 5 ml. of the attenuated strain of TGE virus vaccine described in Example 1. The Group 2 animals, consisting of 4 sows, were inoculated intramuscularly 42 days pre-farrowing and intranasally 14 days pre-farrowing with 5 ml. of the same vaccine used for both intramuscular inoculations of Group 1. The Group 3 control animals, consisting of 3 sows, were not vaccinated. Samples of serum (20 ml.) were taken from each sow 42 days pre-farrowing (prior to the first inoculation of Groups 1 and 2), 14 days pre-farrowing and on the day of farrowing. From each sow of Groups 1, 2 and 3, the serum samples taken 42 days pre-farrowing, 14 days pre-farrowing and on the day of farrowing were used to determine the titers of the TGE virus neutralizing activity in vitro using the standard test of Paul et al referred to in Example 1. The results are reported in Table II as group averages.

TABLE II

Titers of TGE Virus Neutralizing Activity In Sow Serum*
Group Averages

| Group (No. of Sows) | Vaccination Route of Sow | 42 Days Pre-Farrowing | 14 Days Pre-Farrowing | Day of Farrowing |
|---|---|---|---|---|
| 1 (4) | (IM-IM)[a] | 0 | 78 | 274 |
| 2 (4) | (IM-IN)[b] | 0 | 69 | 296 |
| 3 (3) | Controls (Non-Vaccinates) | 0 | 6 | 10 |

*Expressed as the reciprocal of the highest dilution that neutralized 213.8 $TCID_{50}$ , , of TGE virus.
[a](IM-IM) = Inoculated intramuscularly twice, 42 and 14 days pre-farrowing.
[b](IM-IN) = Inoculated intramuscularly 42 days pre-farrowing and intranasally 14 days pre-farrowing.

Samples of colostrum and/or milk (50 ml.) were collected from each sow on the day of farrowing and on days two, four and seven post-farrowing. From each sow of Groups 1, 2 and 3 the colostrum and/or milk samples taken on the day of farrowing and two, four and seven days post-farrowing were used to determine the titers of the TGE virus neturalizing activity using the standard test of Paul et al referred to in Example 1. The results are reported in Table III as group averages.

TABLE III

Titers of TGE Virus Neutralizing Activity
in Pooled Colostrum and/or Milk*
Group Averages

| Group (No. of Sows) | Vaccination Route of Sow | Day of Farrowing | Days Post-Farrowing 2 | 4 | 7 |
|---|---|---|---|---|---|
| 1 (4) | (IM-IM)[a] | 166 | 83 | 62 | 27 |
| 2 (4) | (IM-IN)[b] | 297 | 187 | 103 | 48 |
| 3 (3) | Controls (Non-Vaccinates) | 24 | 23 | 18 | 17 |

*Expressed as the reciprocal of the highest dilution that neutralized 251.2 $TCID_{50}$ , , of TGE virus.
[a](IM-IM) = Inoculated intramuscularly twice, 42 and 14 days pre-farrowing.
[b](IM-IN) = Inoculated intramuscularly 42 days pre-farrowing and intranasally 14 days pre-farrowing.

From Table III it is readily observable that the titers were higher in the Group 2 sows inoculated by the combination intramuscular intranasal route and declined less rapidly than the titers in the Group 1 sows inoculated by the intramuscular intramuscular route.

All piglets born to the sows of Groups 1, 2 and 3 were challenged orally at 48 hours of age with 100 $LD_{50}$ , s of the Purdue strain of TGE challenge virus. Daily during the first 16 days of life the piglets were individually observed for mortality and morbidity (as manifested by signs of diarrhea). The piglets were corraled with their respective dams from farrowing through the post-challenge period and permitted to suckle ad libitum. The results of the mortality and morbidity observations are reported in TAble IV.

TABLE IV

Mortality and Morbidity of Nursing Piglets During
Two Week Post-Challenge Period

| Group (No. of Sows) | Vaccination Route of Sow | % Mortality | % Morbidity[c] |
|---|---|---|---|
| 1 (4) | (IM-IM)[a] | 32 (9 out of 28) | 11 (46/433) |
| 2 (4) | (IM-IN)[b] | 11 (4[d] out of 35) | 4 (24/608) |
| 3 (3) | Controls (Non-Vaccinates) | 100 (21 out of 21)[e] | 53 (48/85) |

[a](IM-IM) = Inoculated intramuscularly twice, 42 and 14 days pre-farrowing.
[b](IM-IN) = Inoculated intramuscularly 42 days pre-farrowing and intranasally 14 days pre-farrowing.
[c]Calculated as piglet days with diarrhea divided by 14 days (the number of days piglets observed post-challenge).
[d]Two out of the four piglet deaths were due to being crushed by the sow. If these two non-TGE related deaths are removed from the calculation the mortality rate is reduced to 6%.
hu e The challenge virus used was highly virulent as shown by 100% mortality for the controls.

From Table IV it will be seen that the incidence of mortality and morbidity in Group 1 piglets, those whose dams were inoculated intramuscularly intramuscularly, was approximately three times greater than the Group 2 piglets, those whose dams were inoculated intramuscularly intranasally.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, or then-present objective to the spirit of this invention without departing from its essential teachings.

What is claimed is:

1. Method of immunizing nursing piglets against transmissible gastroenteritis (TGE) virus by administering to a pregnant sow an effective amount of a vaccine containing attenuated tissue cultured propagated TGE virus, said vaccine being administered twice, (a) intramuscularly at from about 63 days to about 21 days pre-farrowing and (b) intranasally at from about 21 days to about 7 days prefarrowing, with the proviso that at least 14 days and not more than 42 days elapse between the intranasal and intramuscular inoculations, and permitting said nursing piglets to suckle said sow.

2. The method of claim 1 wherein the vaccine is administered (a) intramuscularly 42 days pre-farrowing and (b) intranasally 14 days pre-farrowing.

3. The method of claim 1 wherein the attenuated vaccine contains at least 10,000 $TCID_{50}$'s of TGE virus.

4. The method of claim 1 wherein the attenuated vaccine contains from about 50,000 to about 1,000,000 $TCID_{50}$'s of TGE virus.

5. The method of claim 1 wherein the attenuated vaccine contains at least 10,000 $TCID_{50}$'s of TGE virus and is administered (a) intramuscularly 42 days pre-farrowing and (b) intranasally 14 days pre-farrowing.

6. The method of claim 1 wherein the attenuated vaccine contains from about 50,000 to about 1,000,000 $TCID_{50}$'s of TGE virus and is administered (a) intramuscularly 42 days pre-farrowing and (b) intranasally 14 days pre-farrowing.

* * * * *